United States Patent [19]

Walruff

[11] Patent Number: 4,854,329

[45] Date of Patent: Aug. 8, 1989

[54] APPARATUS AND METHOD FOR NONINVASIVE TESTING OF VOLUNTARY AND INVOLUNTARY MOTOR RESPONSE PATTERNS

[76] Inventor: James C. Walruff, 3638 W. Villa Rita Dr., Phoenix, Ariz. 85308

[21] Appl. No.: 75,955

[22] Filed: Jul. 21, 1987

[51] Int. Cl.$^4$ ............................................... A61B 5/00
[52] U.S. Cl. ..................................... 128/745; 340/576
[58] Field of Search ....................... 128/745, 741, 905; 340/573–576; 351/205–206

[56] References Cited

U.S. PATENT DOCUMENTS

| 3,598,107 | 8/1971 | Ishikawa et al. | 128/745 X |
| 3,777,738 | 12/1973 | Sugita et al. | 128/745 X |
| 3,782,364 | 1/1974 | Watt | 128/745 |
| 3,810,457 | 5/1974 | Bottcher et al. | 128/741 |
| 3,886,540 | 5/1975 | Sussman et al. | 128/745 X |
| 3,913,086 | 10/1975 | Adler et al. | 340/576 |
| 4,004,290 | 1/1977 | Kobayashi et al. | 340/576 X |
| 4,166,452 | 9/1979 | Generales | 128/745 X |
| 4,641,349 | 2/1987 | Flom et al. | 351/206 X |
| 4,723,625 | 2/1988 | Komlos | 340/576 X |

FOREIGN PATENT DOCUMENTS 0149309  7/1981  Fed. Rep. of Germany ...... 128/745

Primary Examiner—Kyle L. Howell
Assistant Examiner—Angela D. Sykes
Attorney, Agent, or Firm—William W. Holloway

[57] ABSTRACT

Apparatus and method are disclosed for providing a noninvasive testing of the status of the motor muscle response of an individual by testing specific voluntary and involuntary motor responses. The voluntary motor response is tested by having the individual under test enter a preselected code sequence (for example, in a keypad) and measuring the parameters associated with the sequence entry. The measured parameters are compared with baseline, non-impaired, parameters for that individual performing the same activity. The involuntary motor response is measured by introducing a transient light stimulus to the pupil of the eye and measuring the response and recovery parameters of the pupil to the light stimulus. The measured involuntary response parameters to the light stimulus is also compared to baseline, non-impaired parameters for the individual responding to the same situation. By comparing measured response parameters to baseline response parameters, non-impairment as an individualized (as contrasted with a statistical) condition can be determined. The tests are positive in nature, in that they designate non-impaired performance of people, identifying impaired persons only be default and not suggesting the source of impairment.

12 Claims, 3 Drawing Sheets

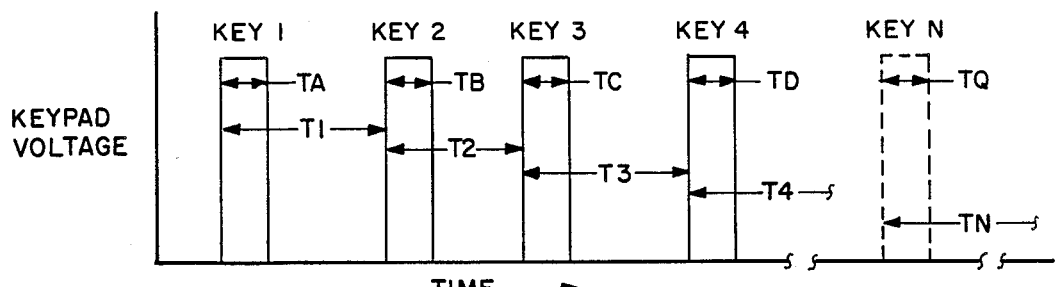
FIG. 3.
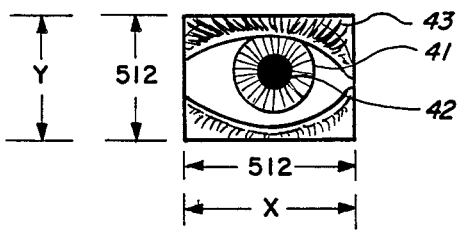
FIG. 4A.
FIG. 4B.
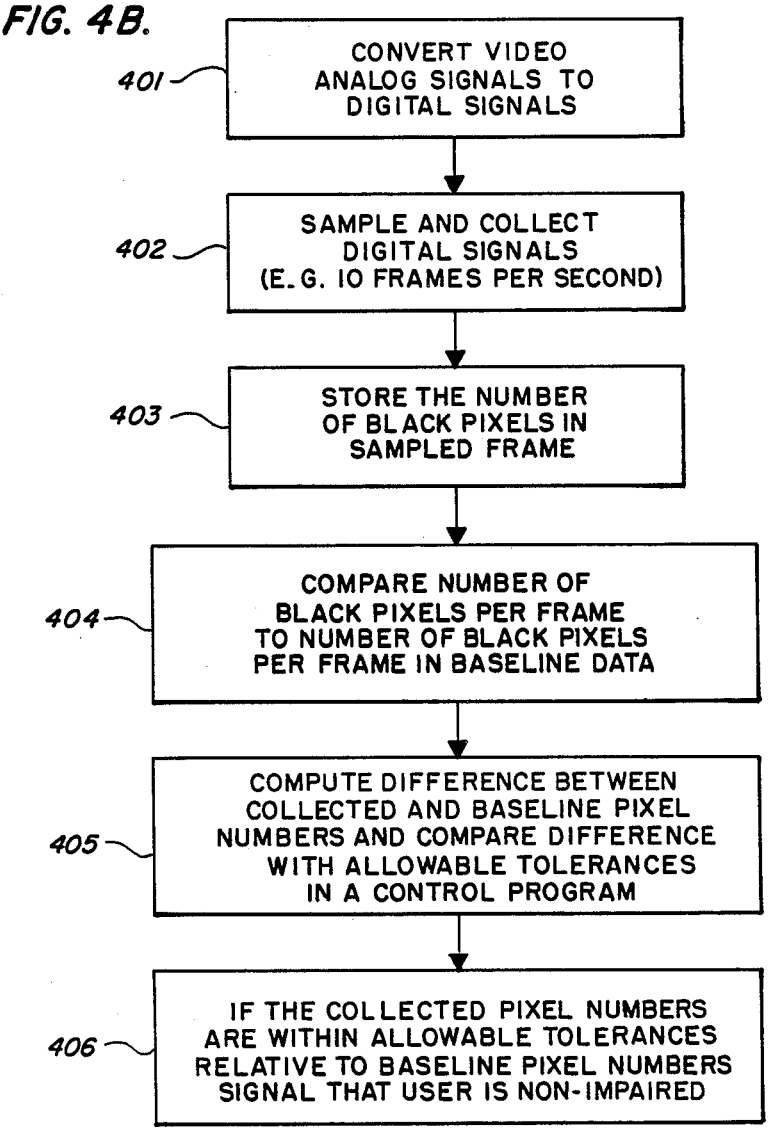

APPARATUS AND METHOD FOR NONINVASIVE TESTING OF VOLUNTARY AND INVOLUNTARY MOTOR RESPONSE PATTERNS

BACKGROUND OF THE INVENTION

1. Field of the Invention

This invention relates generally to the testing of selected motor muscle responses for the purpose of determining that the ability of an individual to perform motor functions has not been impaired. The selected motor responses tested are used as indicators of the overall performance of an individual.

2. Description of the Related Art

The unimpaired performance of employees on the job is a condition that employers have a right to expect and, in some cases, are liable when impaired performance results in loss or injury. Existing technology has not enabled a consistent, non-judgmental and accurate method of assuring that the performance of an individual is unimpaired.

Specifically, the problems associated with determining what persons are performing without impairment are:

a. the belief that impairment of performance is the result only of substance use (e.g. drugs or alcohol).
b. no statistical criteria has been established indicating the quantity of many substances that cause impairment in an individual.
c. the physiological indications of impairment can be so subtle that they are not available to human observers or are subject to differing interpretations.
d. certain legitimate substances that do not cause impairment (e.g. Advil), mimic and are mistaken for substances that do cause impairment (e.g. marijuana).
e. certain testing methods are invasive and may violate constitutional considerations such as "due process" in cases of illegal substances and may violate certain religious beliefs.

While this list does not exhaust the possible list of problems that employers are encountering in this area, it does demonstrate the need for apparatus and method of testing to insure the non-impaired performance of their employees by non-intrusive techniques.

FEATURES OF THE INVENTION

It is an object of the present invention to provide an improved technique for measuring the status of motor muscle response in individuals.

It is a feature of the present invention to identify those individuals capable of unimpaired performance of motor skills and by default, identify those individuals who are impaired and cannot adequately perform motor skills.

It is another feature of the present invention to make precise measurements of voluntary and involuntary motor response patterns.

It is yet another feature of the present invention to compare current measurements for voluntary and involuntary motor responses to known "unimpaired" measurements of voluntary and involuntary motor responses for the individual and, based on a comparison of the current and unimpaired measurements in combination with a predetermined tolerance range, identify whether the individual is impaired or not.

It is a more particular feature of the present invention to determine the status of the voluntary motor response in an individual by use of parameters associated with entry of a selected sequence of numbers in a key pad.

It is yet another more particular object of the present invention to determine the status of the involuntary motor response of an individual by response of the pupil of the eye to a transient light stimulus.

SUMMARY OF THE INVENTION

The aforementioned and other features are accomplished, according to the present invention, by measuring parameters associated with the entry of preselected data into a manual input unit and by measuring the response of the pupil to a pulse of light for an individual. The data entry activity measures voluntary motor response, while the reaction of the pupil to a momentary stimulus measures involuntary motor response. The parameters associated with these activities are compared with baseline parameters measured when the individual was in a non-impaired state. The baseline and the current parameters are compared automatically based on predetermined criteria of non-impairment. Based on the results of the automatic comparison, impairment can be determined on a non-judgmental, but individualized procedure.

These and other features of the present invention will be understood upon reading of the following description along with the drawings.

BRIEF DESCRIPTION OF THE DRAWINGS

FIG. 3 illustrates a set of parameters that can be used to measure the voluntary motor response.

FIGS. 4a and 4b illustrate the technique for testing the involuntary motor response according to the present invention.

DESCRIPTION OF THE PREFERRED EMBODIMENT

1. Detailed Description of the Figures

Figure 1:
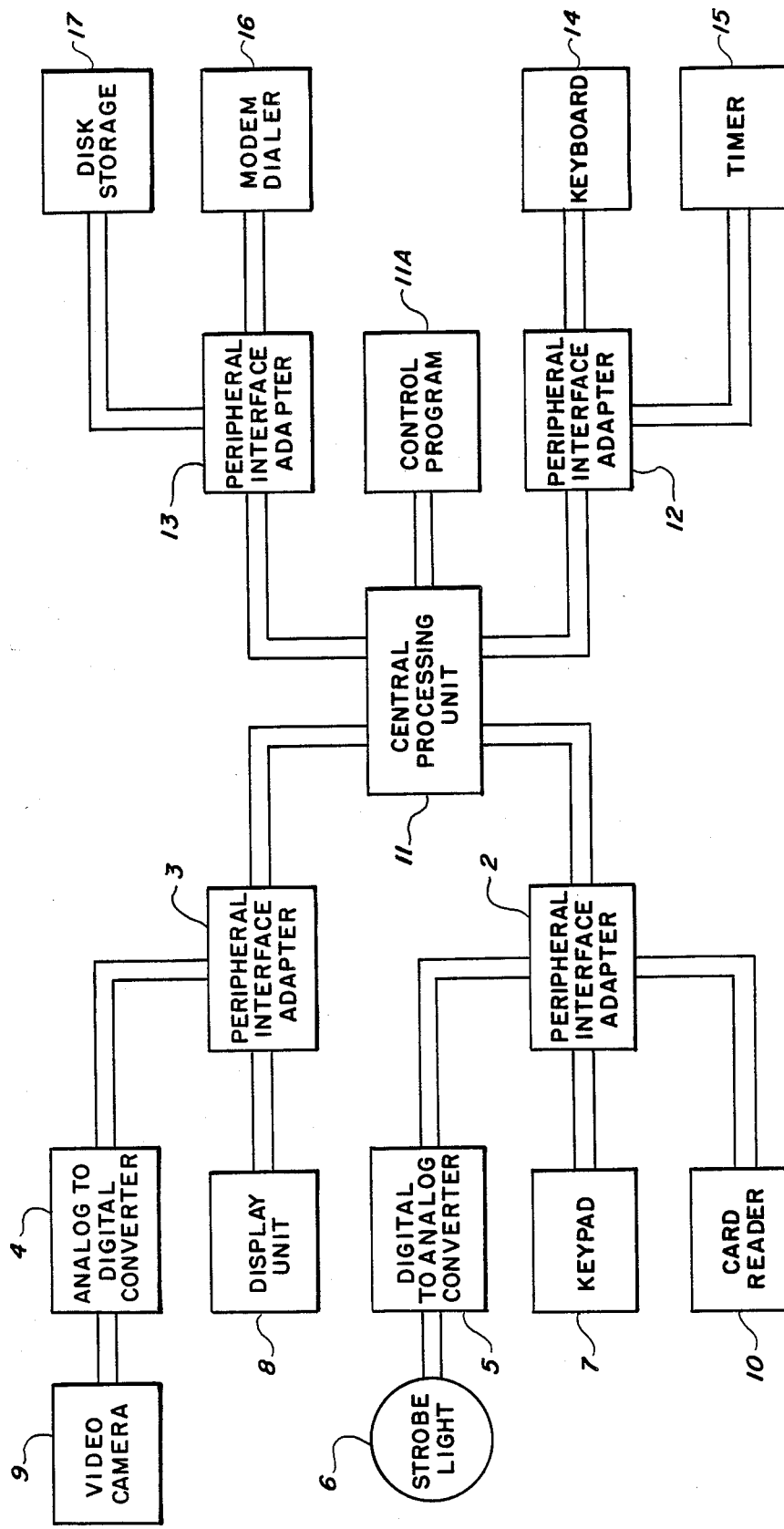
FIG. 1 is a block diagram of the apparatus for testing non-impairment of the motor responses according to the present invention.

Referring to FIG. 1, the central processing unit 11, in response to the control program 11A, determines the data processing activity performed in the testing procedures and controls the activity of the testing apparatus. Video camera 9, in response to optical images, applies signals to analog to digital converter 4. Analog to digital converter 4 applies signals to peripheral interface adapter unit 3. The peripheral interface adapter units 2, 3, 12 and 13 provide the apparatus for temporary storage of logic signals to be exchanged with the central processing unit 11 and for reformatting the signals into an appropriate format during the transfer. In response to signals from the central processing unit 11, peripheral interface adapter unit 3 applies signals to a display unit 8 and to analog to digital converter 4. Digital to analog converter 5 applies signals to the strobe light 6. Keypad 7 and card reader 10 apply signals to peripheral interface adapter unit 2. Disk storage unit 17 and modem dialer 16 exchange signals with peripheral interface adapter unit 13. Keyboard 14 and timer unit 15 apply signals to peripheral interface adapter unit 12. The keyboard 14 permits the system manager to access the control program 11a to encode the baseline data into the personal cards as well as other control and apparatus checking functions. Timer unit 15 provides timing and dating function for the system. The disk storage unit 17 provides mass storage of information such as records of tests, etc. The modem dialer 16 permits communication of the testing system of the present invention with remote locations for exchange of information, diagnostic procedures and similar type functions.

Figure 2:
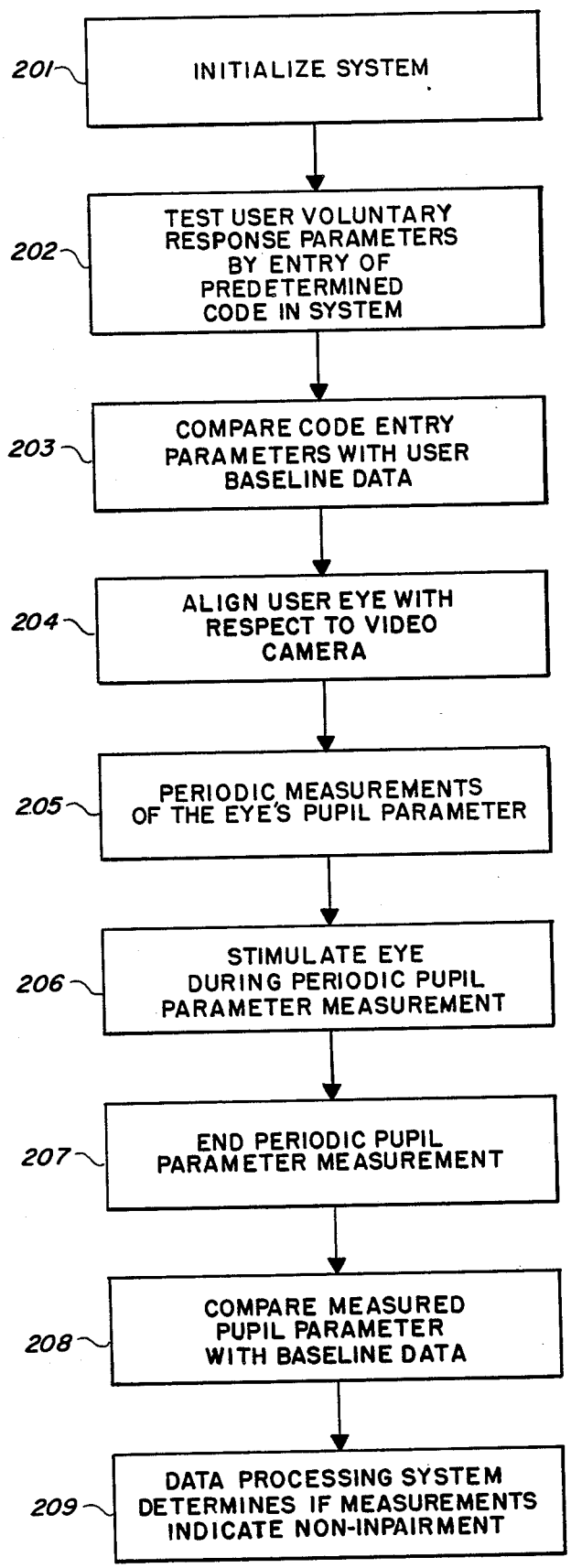
FIG. 2 is a flow diagram of the procedure for using the testing apparatus to determine non-impairment of the voluntary and involuntary motor responses using the apparatus of FIG. 1 according to the present invention.

Referring next to FIG. 2, the procedure for using the apparatus of Claim 1 to determine voluntary and involuntary motor response non-impairment is illustrated. In step 201 the system is initialized. In the preferred emobdiment, the initialization is caused by the insertion of an information-bearing card into the card reader 10. The information on the card identifies the user of the system. In addition, the information on the card can communicate to the system a user identification number and baseline data to be used later. In the alternative, the identification of the user can result in the data files, in the central processing unit or available thereto, associated with the user being made available during test procedures. In step 202, typically in response to a cue on display unit 8, the user will enter his identification code into the data processing system via keypad 7. The central processing unit 11 records both the identification number and parameters associated with the entry of the digits. this information is compared with baseline information associated with the performance of the same activity by the user and a determination is made as to whether the voluntary motor response is impaired relative to the baseline data in step 203. It will be clear that step 202 can be used to initialize the system. However, the independent verification of the identification number is not available and the files related to the baseline performance can not be retrieved until the user number has been entered into the system. In step 204, typically in response to instructions displayed on display unit 8, the user will position his eye in an established relationship with video camera 9. When the eye of the user is properly positioned, the camera provides periodic digitized images of the eye, through the analog to digital converter 4, to the central processing unit in step 205. After the periodic images have begun, a strobe or flash of light is applied to the eye in step 206. The response of the eye to the brief illumination continues to be periodically recorded by the video camera 9 until a steady state condition has been achieved in step 207. In step 208, the images of the eye are analyzed and compared against baseline data. Then based on criteria that are included in the program of the central processing unit 11, a decision is made, in step 209, by the data processing system as to the condition of the user's motor responses and, consequently, as an indicator of the user's ability to execute his assigned duties without impairment.

Referring to FIG. 3, a set of parameters, related to the voluntary motor response, that can be obtained by the entry of a data sequence, such as an identification number, by means of a keypad is illustrated. The time interval T1 is the interval measured between the depression of Key 1 (the entry of the first data sequence element) and the depression of Key 2 (the entry of the second data sequence element). Similarly, the interval T2 is the interval measured between the depression of Key 2 and the depression of Key 3. T3, T4, etc., as desired, are similarly measured. In addition, the interval during which the key is depressed, i.e., TA, TB, etc., is also measured and can be used to identify patterns in the data sequence entry. In the preferred embodiment, a four element data sequence is employed. However, the use of N digits (keys) can be used.

Referring to FIGS. 4A and 4B, the technique for determining parameters of the involuntary motor response is illustrated. In the preferred embodiment, the response of the pupil to a pulse of light is used as the involuntary response indicator. The eye is positioned relative to video camera 9 in such a manner that the pupil 41 and the surrounding iris 42 occupies an appreciable portion of the image frame. The video camera senses the regions of the image in a $512 \times 512$ array of pixels (i.e., image points). Associated with each pixel are three colors (typically red, green and blue) and the video camera determines the intensity parameters of each color component for each pixel in step 401. The output signals from the video camera are typically in analog form and must be converted to digital format (via analog to digital converter (in step 402. In the data processing system, the digitized pixel parameters are compared against a reference parameter group (i.e., defining a black pixel) in step 403. In step 404, the number of pixels for each frame that meets the reference criteria are stored for each frame.

2. Operation of the Preferred Embodiment

Voluntary and involuntary motor responses can be established in a noninvasive manner through the entry of a signal group into a keypad for the voluntary motor response and by observation of the response of the (pupil of the) eye to a light strobe for the involuntary motor response. The determination of non-impairment is performed by predetermined criteria, and is not the result of a judgment by an observer. In addition, the present invention tests the actual motor function and does not rely on presence or absence of some substance to imply impairment. In addition, the test is individualized in the sense that the motor response parameters are compared to parameters of the individual currently undergoing the testing procedure. At some predetermined time, the parameters of the user are measured and the results of this measurement are used to establish the (unimpaired) baseline data against which the current testing procedure is compared. The only judgment results from the criteria entered into the data processing system wherein the determination is made as to the amount of departure from the baseline parameters to be interpreted as unacceptable impairment. Indeed, this criteria can vary from individual to individual depending on the level of performance required by the individual (or user) to execute the assigned activity. With respect to the voluntary response parameters of FIG. 3, these parameters can be used not only per se, but can also be used to form selected ratios in order to provide a better indication of the motor response than can be obtained by the intervals between the digit entry measured by T1, T2, T3 etc. The ratios can be used in identifying patterns, specific to the individual, in the entry of a data sequence.

Productivity, quality and safety in the work place require the unimpaired performance of each individual worker. Employers depending on current technology to guard against impairment have experienced haphazard and random results as well as considerable resistance from workers. The present invention elicits little or no resistance and consistent reliable results.

The testing system of the present invention utilizes current data regarding the individual compared to baseline (unimpaired) data from the same individual, and does not use potentially ambiguous statistical generalizations. The combined use of voluntary and involuntary response patterns enhances reliability of the testing procedure. The pupillary and hand-eye response patterns have historically been implemented by physicians and psychologists as adequate representations of general neurological impairment. That history combined with the enhanced ability to make refined measurements and comparisons assure the usefulness of this invention in the work place.

Referring once again to FIGS. 4A and 4B, the reference parameter used by the data processing system is for the color black. The pupil, being black, will therefore be included in the accumulation of the number of pixels meeting the reference criteria. In addition, other black objects such as eyelashes will also be included in the accumulation. However, the contribution of other black objects in the image frame will be irrelevant as they will not change and it is change that is being measured. Using this technique, small movements of the eye (e.g., because of movements of the head) will not effect the resulting accumulation of the number of black pixels. In the preferred embodiment, an image frame is examined every tenth of a second for six seconds, the six seconds including the time of the light pulse. Using the accumulated number of black pixels for the 600 frames examined by the data processing system, the contraction of the pupil as a result of the light strobe and the recovery can be plotted as a function of time. The decay curve, resulting from stimulation and recovery of the eye, can be used to compare the involuntary motor response currently available to the user with the baseline motor response.

One use of the present invention is to use successful completion of the non-impairment activity as a requirement for entry into the work place. In the preferred embodiment, the entry procedure is completely automated.

In the preferred embodiment, provision is made for repetition of the test procedure a preselected number of times. After that number of test procedures has been performed, a response can be selected, preventing a retry of the test procedure for a chosen period of time.

The foregoing description is included to illustrate the operation of the preferred embodiment and is not meant to limit the scope of the invention. The scope of the invention is to be limited only by the following claims. From the foregoing description, many variations will be apparent to those skilled in the art that would yet be encompassed by the spirit and scope of the invention.

What is claimed is:

1. Testing apparatus for on-site testing of motor response impairment of a subject, wherein voluntary and involuntary response baseline parameters along with an identification code are stored on a data card suitable for convenient conveyance by said subject, said testing apparatus comprising:

data entry means for manually entering data in said testing apparatus, said subject entering subject code in said testing apparatus by means of said data entry means;

voluntary response means for measuring voluntary response parameters resulting from manipulation of said data entry means according to a predetermined pattern;

involuntary response means for measuring involuntary response parameters associated with changes in a pupil of said eye resulting from a transient light stimulus;

card reading means for entering data from said data card into said apparatus; and comparison means for comparing said subject code with said identification code; a positive comparison between said subject code and said identification code permitting further operation of said comparison means, said comparison means for comparing said voluntary and involuntary response baseline parameters stored on said data card with measured voluntary and involuntary response parameters from said voluntary response means and said involuntary response means, said comparison means providing a signal indicating when said subject's voluntary and involuntary response parameters meet preselected criteria without operator intervention.

2. The motor response impairment testing apparatus of claim 1 wherein said comparison means includes means for said preselected criteria in said comparison means, said preselected criteria determining allowable tolerances between said voluntary and involuntary baseline response parameters and said voluntary and involuntary measured response parameters.

3. The motor response impairment testing apparatus of claim 2 wherein said measured voluntary parameters associated with said data entry means include timing parameters associated with activation of a predetermined sequence of entry units associated with said data entry means, said measured voluntary response parameters and said baseline response parameters including patterns of said predetermined sequence activation.

4. The motor response impairment testing apparatus of claim 2 wherein said involuntary response means includes a color video unit, said color video unit automatically determining a number of pixels of a video image having a preestablished color, wherein an area of said pupil is determined by a total number of pixels having said preestablished color, said involuntary response means including apparatus for measuring an area of said pupil as a function of time.

5. The motor response impairment testing apparatus of claim 4 further comprising a display means, said display means receiving preestablished signals from said testing apparatus for coordinating activity of said subject during an impairment test procedure.

6. The method of on-site testing of nonimpairment of motor muscle activity by a subject, said method comprising the steps of:

testing an involuntary motor response of a subject as a function of time when said involuntary motor response is nonimpaired;

storing a first set of time dependent parameters resulting from said testing of said involuntary motor response on a data card, said data card including subject identification data;

testing a voluntary motor response of said subject as a function of time when said voluntary motor response is nonimpaired;

storing a second set of time dependent parameters resulting from said voluntary motor response testing on said data card;

transferring said first and said second set of response parameters and said identification data from said data card to an on-site testing apparatus;

comparing said identification data with data entered manually in said test apparatus to confirm a relationship between said data card and said subject;

repeating said involuntary motor response testing step by said subject by means of said on-site testing apparatus and generating a third set of time dependent parameters derived therefrom;

comparing said first set of parameters with said set of parameters without operator intervention;

repeating said voluntary motor response testing step by said subject by means of said on-site testing apparatus and generating a fourth set of time dependent parameters derived therefrom;

comparing said second set of parameters with said fourth set of parameters without operator intervention; and indicating nonimpairment of said subject's involuntary motor response when said relationship is confirmed, said first and said third set of time dependent parameters are within specified tolerances and said second and said fourth set of time dependent parameters are within preselected tolerances.

7. The method of on-site testing for nonimpairment of motor response activity of claim 6 wherein said involuntary motor response testing step and said repeating said involuntary motor response testing step include the step of determining a number of pixels having a color of a subject's pupil as a function of time in response to transient light stimulus.

8. The method of on-site testing for nonimpairment of motor response activity of claim 6 wherein the step of testing a voluntary motor response includes the step of measuring parameters associated with entering preselected data by means of a manual entry device in a data processing system, said second and said fourth sets of parameters including parameters relating to time dependent patterns for activation of preselected manual entry units.

9. Testing apparatus for on-site testing for nonimpairment of motor muscle response of a subject, said apparatus comprising:

card storage means for storing subject identification data, subject involuntary motor response baseline nonimpaired paramenters and subject voluntary motor response baseline and nonimpaired parameters;

card reading apparatus for transferring said subject identification data, said involuntary response baseline parameters and said voluntary response baseline parameters to said testing apparatus;

stimulus means for providing a transient stimulus to a pupil of an eye of said subject;

first measuring means for measuring a first set of parameters associated with a time varying response of said pupil to said transient stimulus, wherein said pupil time varying response is determined by a time dependent of a number of pixels having a color of said pupil;

keyboard entry means for entering data manually in said testing apparatus, wherein said subject enters code data related to said subject identification number;

second measuring means for measuring a second set of parameters determined by measuring a time dependent of activation of a preselected sequence of key units of said keyboard entry means;

comparison means for comparing said first set of parameters with said involuntary response parameters, comparing said second set of said parameters with said voluntary response parameters and for comparing said subject identification data with said code data; and indicator means for indicating when said first set of parameters and said involuntary response parameters, said second set of parameters and said voluntary response parameters and said code data and said subject identification data have predetermined relationships.

10. The testing apparatus for on-site testing for motor response nonimpairment of a subject of claim 9 wherein said comparison means can have tolerance parameters entered therein, said comparison means indicating to said indicator means when said first set of parameters is within said tolerance parameters of said involuntary response parameters.

11. The testing apparatus for on-site testing for motor response nonimpairment of claim 9 wherein said apparatus further comprises a data processing means and a display means for providing said subject with instructions for executing on-site testing procedures.

12. The testing apparatus for on-site testing for motor response nonimpairment of claim 11 wherein said apparatus further comprises activation means for initiating activity in said stimulus means, said first measuring means, said second measuring means, said comparison means and said indicator means.

* * * * *